United States Patent [19]

Blickle et al.

[11] Patent Number: 4,985,594
[45] Date of Patent: Jan. 15, 1991

[54] PROCESS FOR THE PREPARATION OF FLUORINATED CARBOXYLIC ACID FLUORIDES

[75] Inventors: Peter Blickle, Taunus; Klaus Hintzer, Burgkirchen; Werner Schwertfeger, Langgöns; Heinz Strutz, Frankfurt am Main, all of Fed. Rep. of Germany

[73] Assignee: Hoechst Aktiengesellschaft, Frankfurt am Main, Fed. Rep. of Germany

[21] Appl. No.: 389,271

[22] Filed: Aug. 3, 1989

[30] Foreign Application Priority Data

Aug. 6, 1988 [DE] Fed. Rep. of Germany ....... 3826808

[51] Int. Cl.$^5$ .............................................. C07C 51/62
[52] U.S. Cl. .................................... 562/851; 568/849; 568/850
[58] Field of Search ........................ 562/849, 850, 851

[56] References Cited

U.S. PATENT DOCUMENTS 2,456,768 12/1948 Chaney ................................ 558/461

FOREIGN PATENT DOCUMENTS 0260713 3/1988 European Pat. Off. .
1668546 9/1971 Fed. Rep. of Germany .
144480 3/1961 U.S.S.R. .

OTHER PUBLICATIONS

R. N. Haszeldine et al., J. C. S., 1968, 398–405.
Abstract of 61-225150, II, No. 63 (C–406) (2510), 2/26/87.
P. Tarrant et al., *Fluor. Chem. Rev.* 5:77–113 (1971).
H. Millauer et al., *Angew. Chem. Int. Ed. Engl.* 24:161–179 (1985).

*Primary Examiner*—Paul J. Killos

[57] ABSTRACT

Process for the preparation of fluorinated carboxylic acid fluorides

Fluorinated carboxylic acid fluorides of the Formula I

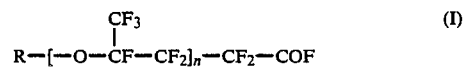

can be prepared from fluorinated vinyl ethers of the Formula II

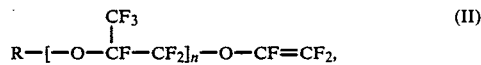

by heating the vinyl ethers to a temperature of 100° to 350° C.

Perfluorinated carboxylic acids and derivatives thereof can be prepared from the carboxylic acid fluorides by secondary reactions, for example hydrolysis, esterification or aminolysis.

9 Claims, No Drawings

PROCESS FOR THE PREPARATION OF FLUORINATED CARBOXYLIC ACID FLUORIDES

The invention relates to the preparation of fluorinated carboxylic acid fluorides from fluorinated vinyl ethers.

Fluorinated carboxylic acids and derivatives thereof have many possible uses in industry. The salts of long-chain perfluorinated carboxylic acids are used as emulsifiers in the preparation of polytetrafluoroethylene, whereas fluorinated carboxylic acids in the form of their acid fluorides are required for synthesis of fluorinated vinylethers. Fluorinated carboxylic acids are converted into the corresponding Kolbe products, which are used as inert liquids or as solvents for fluorinated resins, and perfluorinated carboxylic acid fluorides are converted into perfluorinated inert liquids by exposure to light.

Fluorinated carboxylic acid fluorides containing ether groups are formed by reactions of fluorinated acid fluorides with fluorinated epoxides, for example hexafluoropropene oxide (HFPO) or tetrafluoroethylene oxide (TFEO). If HFPO is used, the products are always branched, whilst TFEO is a substance which is difficult to prepare and handle (compare H. Millauer et al., Angew. Chem., Int. Ed. Engl. 24 (1985) 161; and P. Tarrant et al., Fluor. Chem. Rev., 5 (1971) 77).

Thermal rearrangement of perfluoromethylvinyl ether $CF_3$—O—$CF=CF_2$ to give perfluoropropionyl fluoride is furthermore described in the literature:

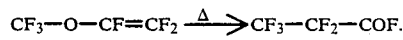

The reaction is carried out with a small amount of vinyl ether in the gas phase at a temperature of 595° C. and gives a yield of 67% of acid fluoride, based on the vinyl ether reacted (compare R. N. Haszeldine et al., J. Chem. Soc. (C), 1968, 398).

It has to date been possible to prepare short-chain perfluoroacyl fluorides only with the aid of metal fluorides as catalysts at elevated temperatures. This applies to perfluoropropionyl fluoride and perfluorobutyryl fluoride (compare EP-A-No. 0,260,713).

There was thus the object of discovering a process for the preparation of straight-chain and branched perfluorinated carboxylic acids and derivatives thereof. The process should start from starting materials which are used industrially and be capable of providing compounds of various structures using only one type of reaction and without using a catalyst.

It has been found that fluorinated vinyl ethers give fluorinated carboxylic acid fluorides by heating to a temperature of 100° to 350° C., it being possible for these products in turn to be converted into fluorinated carboxylic acids and derivatives thereof.

The invention thus relates to the process as claimed in the claims.

Fluorinated carboxylic acid fluorides of the Formula I $$R-[-O-\underset{\underset{CF_3}{|}}{CF}-CF_2]_n-CF_2-COF \quad (I)$$

in which R denotes a branched or straight-chain perfluorinated radical having 1-10, preferably 1-7, carbon atoms, in which one or more fluorine atoms can be replaced by other halogen atoms or hydrogen or another functional group, for example $COOR^4$ ($R^4$=alkyl), —$SO_2F$ and —CN, and n is an integer from zero to 10, preferably from one to 5 and in particular 1 or 2, are prepared from vinyl ethers of the Formula II

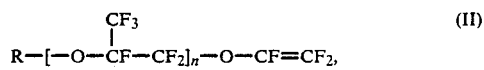

where R and n are as in Formula I, by heating to a temperature of 100° to 350° C., preferably 150° to 300° C.

The reaction of the vinyl ether of the Formula II is preferably carried out in a pressure-resistant vessel, for example in an autoclave under the intrinsic pressure or under normal pressure, preferably under the intrinsic pressure. Because of the risk of an explosive reaction of the substances with oxygen, the reaction is carried out under an inert gas atmosphere, preferably nitrogen or argon. The reaction can also be carried out in an inert halogenated solvent, such as, for example, $CF_2Cl$—$CFCl_2$ and $CCl_4$ or perfluorinated ethers.

The progress of the reaction is monitored by removing samples and analyzing these samples by gas chromatography or infrared spectral analysis.

After the reaction, the products can be converted into their corresponding carboxylic acids or derivatives thereof, for example esters and amides, preferably esters, by secondary reactions, for example hydrolysis, esterification or aminolysis, preferably esterification.

The reaction according to the invention enables fluorinated acid fluorides or ketones with various substituents to be lengthened by two carbon atoms in accordance with the following equations:

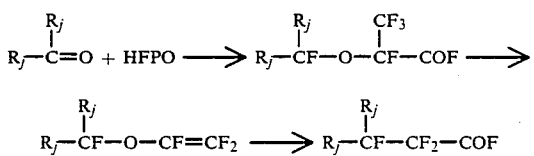

where $R_j$ and $R_j' =$ F or a fluorinated radical.

EXAMPLES

Example 1

150 g of $CF_3$-$CF_2$-$CF_2$-O-$CF=CF_2$ were initially introduced into a stainless steel 200 cm³ autoclave. The autoclave was then flushed with nitrogen and heated at 200°-230° C. for 6 hours.

After the autoclave had cooled to room temperature, 30 cm³ of methanol were introduced into the autoclave, while cooling with ice. After the contents of the autoclave had been washed with water, 141 g of organic phase were obtained, which, according to the gas chromatogram (WLD), contained 68% of $CF_3$-$CF_2$-$CF_2$-$CF_2$-$COOCH_3$.

Example 2

A mixture of 80 cm³ of $CF_2Cl$-$CFCl_2$ and 80 g of $CF_3$-$CF_2$-$CF_2$-O-$CF=CF_2$ was heated at 225° C. in the apparatus described under Example 1 for 4 hours. The product mixture was then esterified with methanol and washed with water. The gas chromatogram of the resulting mixture showed 66% of CF$_2$Cl-CFCL$_2$
21% of CF$_3$-CF$_2$-CF$_2$-CF$_2$-COOCH$_3$ and
5% of CF$_3$-CF$_2$-CF$_2$-O-CF=CF$_2$.
Distillation of the ester gave a yield of 30 g, and the ester here had a boiling point of 102°–106° C.

Example 3

150 g of the Formula

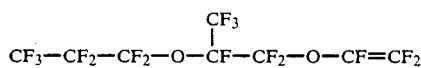

were heated at 200°–215° C. in the autoclave of Example 1 for 3 hours.

The contents of the autoclave (149 g) were distilled. 68 g of a colorless liquid which, according to the $^{19}$F-NMR spectrum, consisted of the formula to the extent of 90%, were obtained at a boiling point of 101°–105° C. The vinyl ether employed was detected as a further component.

The yield of the acid fluoride was 41%.

Example 4

130 ml of the perfluoropolyether

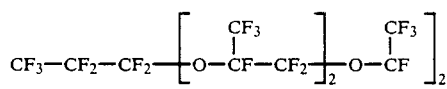

were initially introduced into a glass flask, which was provided with a magnetic stirrer, thermometer, inlet tube with frit, packed column and column head, such that the frit was immersed completely. The apparatus was then heated up to an internal temperature of 215° to 225° C. 89 g of the ether described in Example 3 were then added by means of a metering pump in the course of 7 hours.

Distillation of the product gave a yield of 66 g. A sample of the distillate was esterified with methanol and analyzed by gas chromatography (WLD). The product contained:

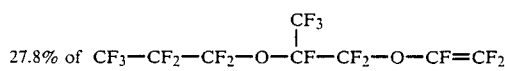

This procedure is suitable for continuous rearrangement of vinyl ethers in the acid fluoride.

EXAMPLE 5

80 g of the vinyl ether from Example 3 were reacted in 80 cm$^3$ of CF$_2$Cl-CFCl$_2$ at 200° C. in the course of 10 hours in accordance with Example 2.

The product was then esterified with methanol and distilled.

The yield of the formula

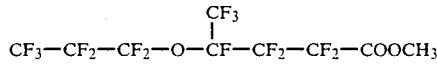

was 42% (35 g) at a boiling point of 58°–62° C./25 mbar.

Example 6

A mixture of 91% by weight of (CF$_3$)$_2$CF-O-CF=CF$_2$ and 9% by weight of CF$_3$-CF$_2$-CF$_2$-O-CF=CF$_2$ was introduced into an NMR tube. The glass tube was sealed by fusion and heated at 150° C. for 3 days. A $^{19}$F-NMR spectrum of the mixture was then recorded with CFCl$_3$ as the external standard. No further vinyl ether was to be detected. (CF$_3$)$_2$CF-CF$_2$-COF was detected as the main component (>70% by weight) with signals at +22.5 ppm (1F, -COF, m), -74.6 ppm (6F, CF$_3$, m), -114.8 ppm (2F, CF$_2$, m) and -188.1 ppm (1F, CF, m).

( 20 Example 7

100 g of Br—CF$_2$—CF$_2$—O—CF=CF$_2$ were heated at 200° C. in the autoclave of Example 1 for 7 hours. The crude product (96 g) was analyzed with the aid of 19F-NMR spectroscopy.

According to this analysis, the crude product contained the vinyl ether Br—CF$_2$-CF$_2$—O—CF=CF$_2$ and the acid fluoride Br—CF$_2$-CF$_2$-CF$_2$—COF in a ratio of 1:2 in addition to other unidentifiable substances.

After esterification with methanol, the ester Br—CF$_2$—CF$_2$—CF$_2$-COOCH$_3$ was isolated by distillation at a boiling point of 73°–76° C./133 mbar.

Example 8

100 g of H—CF$_2$—CF$_2$—CF$_2$—O—CF=CF$_2$ were heated at 200° C. in the autoclave of Example 1 for 24 hours. After cooling to room temperature, the contents of the autoclave were esterified with 30 cm$^3$ of methanol. The product mixture was worked up by washing with water and drying over Na$_2$SO$_4$.

98 g of organic liquid were obtained, and were analyzed with the aid of gas chromatography. According to this analysis, the substance mixture contained 43% of H—(CF$_2$)$_4$—COOCH$_3$.

Example 9

100 g H-(CF$_2$)$_5$—O—CF=CF$_2$ were heated at 250° C. in the autoclave of Example 1 for 20 hours.

Working up was carried out in accordance with Example 5. Distillation gave a yield of H-(CF$_2$)$_6$—COOCH$_3$ of 33 g. The boiling point of the ester was 107°–108° C./133 mbar.

Example 10

44.6 g (0.1 mole) of

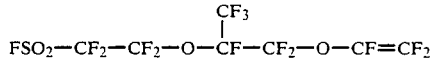

were initially introduced into the apparatus of Example 7, the apparatus was flushed with argon and the contents were heated under reflux (internal temperature of 132°–133° C.) for 12 hours. A sample taken from the liquid phase showed only a weak acid fluoride band in the IR spectrum. 50 ml of the perfluorinated polyether

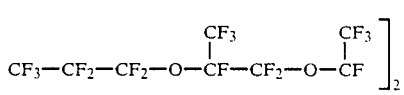

were added as an inert solvent and the batch was heated again under reflux for 6 hours. The internal temperature was 170° C.

Thereafter, no further vinyl ether was detectable in the IR spectrum of a sample from the liquid phase. Distillation gave 17 g of a colorless liquid, at a boiling point of 134°–144° C., which, according to the $^{19}$F-NMR spectrum, consisted of

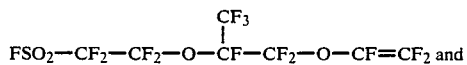

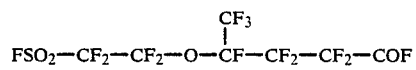

in a molar ratio of 1:2.2.

Further distillation gave a fraction (10 g) with a boiling point of 144°–213° C., which, according to the $^{19}$F-NMR spectrum, consisted of

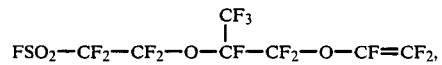

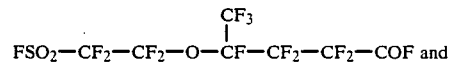

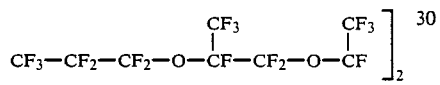

in a molar ratio of 1.5:5.2:1.

Example 11

15 g of the formula

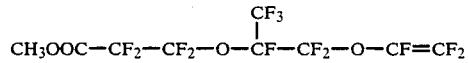

were initially introduced into a glass flask fitted with a magnetic stirrer, thermometer, gas inlet tube and reflux condenser with a bubble counter attached, and the apparatus was flushed with nitrogen. The batch was heated under reflux. During this heating, the bottom temperature rose from 159° C. to 182° C. in the course of 8 hours. A $^{19}$F-NMR spectrum of the reaction mixture was recorded, and showed a conversion of the vinyl ether of more than 80%. Distillation gave a fraction (3 g) with a boiling point of 49° C./13 mbar, which, according to the $^{19}$F-NMR spectrum, contained the compounds

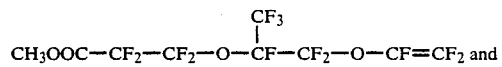

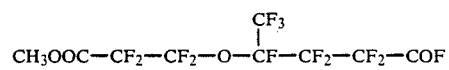

in a molar ratio of 1:2.2, in addition to small amounts of impurities.

Example 12

100 g of the perfluoropolyether

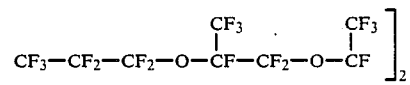

and 10 g H—(CF$_2$)$_3$—O—CF—CF$_2$—O—CF=CF$_2$ were initially introduced into the apparatus of Example 11 and the batch was heated up to an internal temperature of about 180° C. in the course of 1.5 hours. The reaction mixture was then distilled until the boiling point of about 200° C. was reached. The distillate (7.3 g) was analyzed with the aid of IR spectroscopy. In addition to a very strong band for the COF group at 1887 cm$^{-1}$, only a very weak band for the vinyl ether group at 1840 cm$^{-1}$ was also obtained.

The experiment was continued by heating the perfluoropolyether which remained at the bottom to 170°–190° C. and adding 95.3 g of H-PPVE-2 dropwise in the course of 11 hours. At the same time, the mixture which boils at 115°–120° C. was distilled off. 83 g of distillate were obtained and were esterified with methanol, washed with water and dried over Na$_2$SO$_4$. A gas chromatogram (WLD) of the esterified product (80 g) was then recorded. It showed the composition:

59.0% of H-PPVE-2

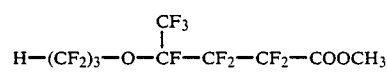

6.8% of perfluoropolyether.

The ester

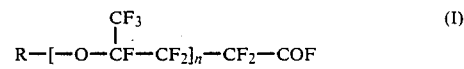

was isolated by distillation at a boiling point of 85° C./67 mbar.

We claim:

1. A process for the preparation of a fluorinated carboxylic acid fluoride of the Formula I

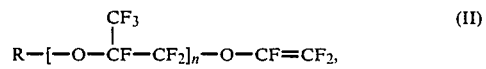

in which R denotes a branched or straight-chain perfluorinated radical having 1–10 carbon atoms, in which one or more fluorine atoms can be replaced by other halogen atoms or hydrogen or another functional group, and n is an integer from zero to 10, which comprises heating a vinyl ether of the Formula II $$R-[-O-\underset{\underset{CF_3}{|}}{CF}-CF_2]_n-O-CF=CF_2, \quad (II)$$

where R and n are as in Formula I, in an inert gas atmosphere or inert halogenated solvent to a temperature of 100° C. to 350° C.

2. The process as claimed in claim 1, wherein the reaction is carried out in a temperature range from 150° C. to 350° C.

3. The process as claimed in claim 1, wherein R denotes a branched or straight-chain perfluorinated radical having 1-7 carbon atoms.

4. The process as claimed in claim 1, wherein said fluorine atoms can be replaced by $COOR^4$, $-SO_2F$ and $-CN$, wherein $R^4$ is an alkyl.

5. The process as claimed in claim 1, wherein n is an integer ranging from 1 to 5.

6. The process as claimed in claim 1, wherein n is an integer of 1 to 2.

7. The process as claimed in claim 1 wherein said heating occurs in the absence of a catalyst.

8. The process as claimed in claim 1, wherein said inert gas is nitrogen or argon.

9. The process as claimed in claim 1, wherein said inert halogenated solvent is $CF_2Cl-CFCl_2$, $CCl_4$ or perfluorinated ethers.

* * * * *